United States Patent
Pederson et al.

(10) Patent No.: US 7,744,574 B2
(45) Date of Patent: Jun. 29, 2010

(54) CATHETER TIP TO REDUCE WIRE LOCK

(75) Inventors: Gary Pederson, Albertville, MN (US); Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 927 days.

(21) Appl. No.: 11/013,956

(22) Filed: Dec. 16, 2004

(65) Prior Publication Data

US 2006/0135979 A1   Jun. 22, 2006

(51) Int. Cl.
    *A61M 25/00* (2006.01)
(52) U.S. Cl. ..................................................... 604/267
(58) Field of Classification Search .............. 604/96.01, 604/267; 606/159, 191
    See application file for complete search history.

(56) References Cited

U.S. PATENT DOCUMENTS

| | | | |
|---|---|---|---|
| 998,339 A * | 7/1911 | Hollins | ........................ 27/24.2 |
| 3,631,848 A | 1/1972 | Muller | |
| 3,911,927 A | 10/1975 | Rich et al. | |
| 3,915,171 A | 10/1975 | Shermeta | |
| 4,085,185 A | 4/1978 | Adair | |
| 4,195,637 A | 4/1980 | Grüntzig et al. | |
| 4,249,536 A | 2/1981 | Vega | |
| 4,251,305 A | 2/1981 | Becker et al. | |
| 4,307,722 A | 12/1981 | Evans | |
| 4,323,071 A | 4/1982 | Simpson et al. | |
| 4,385,635 A | 5/1983 | Ruiz | |
| 4,413,989 A | 11/1983 | Schjeldahl et al. | |
| 4,425,919 A | 1/1984 | Alston, Jr. et al. | |
| 4,531,512 A | 7/1985 | Wolvek et al. | |
| 4,531,943 A | 7/1985 | Van Tassel et al. | |
| 4,540,404 A | 9/1985 | Wolvek | |
| 4,551,292 A | 11/1985 | Fletcher et al. | |
| 4,571,240 A | 2/1986 | Samson et al. | |
| 4,588,399 A | 5/1986 | Nebergall et al. | |
| 4,596,563 A | 6/1986 | Pande | |
| 4,610,662 A | 9/1986 | Weikl et al. | |
| 4,636,272 A | 1/1987 | Riggs | |
| 4,636,346 A | 1/1987 | Gold et al. | |

(Continued)

FOREIGN PATENT DOCUMENTS

AU         64747/94 A         3/1995

(Continued)

OTHER PUBLICATIONS

*Plastics Digest*, Edition 15, vol. 2, 1994, p. 2-314.

(Continued)

*Primary Examiner*—Nicholas D Lucchesi
*Assistant Examiner*—Aarti B Berdichevsky
(74) *Attorney, Agent, or Firm*—Crompton, Seager & Tufte, LLC

(57) ABSTRACT

An elongate medical device and methods for making and using the same. The elongate medical device may be a catheter that includes an elongate tubular shaft having a lumen defined therein. A scraping member is coupled to an inner wall surface of the shaft and extends into the lumen. The scraping member is configured to remove debris that may build up or otherwise be disposed on another medical device such a guidewire.

16 Claims, 5 Drawing Sheets

U.S. PATENT DOCUMENTS

| | | | |
|---|---|---|---|
| 4,646,719 A | 3/1987 | Neuman et al. | |
| 4,676,229 A | 6/1987 | Krasnicki et al. | |
| 4,706,670 A | 11/1987 | Andersen et al. | |
| 4,739,768 A | 4/1988 | Engelson | |
| 4,748,982 A | 6/1988 | Horzewski et al. | |
| 4,753,765 A | 6/1988 | Pande | |
| 4,759,748 A | 7/1988 | Reed | |
| 4,764,324 A | 8/1988 | Burnham | |
| 4,782,834 A | 11/1988 | Maguire et al. | |
| 4,790,812 A * | 12/1988 | Hawkins et al. | 604/22 |
| 4,808,164 A | 2/1989 | Hess | |
| 4,817,613 A | 4/1989 | Jaraczewski et al. | |
| 4,819,751 A | 4/1989 | Shimada et al. | |
| 4,820,349 A | 4/1989 | Sabb | |
| 4,863,442 A | 9/1989 | DeMello et al. | |
| 4,884,573 A | 12/1989 | Wijay et al. | |
| 4,886,506 A | 12/1989 | Lovgren et al. | |
| RE33,166 E | 2/1990 | Samson | |
| 4,898,896 A | 2/1990 | Maj et al. | |
| 4,906,244 A | 3/1990 | Pinchuk et al. | |
| 4,917,666 A | 4/1990 | Solar et al. | |
| 4,323,071 A | 5/1990 | Simpson et al. | |
| 4,921,483 A | 5/1990 | Wijay et al. | |
| 4,943,278 A | 7/1990 | Euteneuer et al. | |
| 4,950,239 A | 8/1990 | Gahara et al. | |
| 4,955,377 A | 9/1990 | Lennox et al. | |
| 4,955,862 A | 9/1990 | Sepetka | |
| 4,960,410 A | 10/1990 | Pinchuk | |
| 4,964,409 A | 10/1990 | Tremulis | |
| 4,964,853 A | 10/1990 | Sugiyama et al. | |
| 4,976,720 A | 12/1990 | Machold et al. | |
| 4,990,139 A | 2/1991 | Jang | |
| 4,994,018 A | 2/1991 | Saper | |
| 4,994,032 A | 2/1991 | Sugiyama et al. | |
| 4,998,923 A | 3/1991 | Samson et al. | |
| 5,002,559 A | 3/1991 | Tower | |
| 5,047,045 A | 9/1991 | Arney et al. | |
| 5,050,606 A | 9/1991 | Tremulis | |
| 5,078,702 A | 1/1992 | Pomeranz | |
| 5,078,727 A | 1/1992 | Hannam et al. | |
| 5,093,546 A | 3/1992 | Matsumiya et al. | |
| 5,100,381 A | 3/1992 | Burns | |
| 5,104,377 A | 4/1992 | Levine | |
| 5,120,308 A | 6/1992 | Hess | |
| 5,122,125 A | 6/1992 | Deuss | |
| 5,139,496 A | 8/1992 | Hed | |
| 5,143,093 A | 9/1992 | Sahota | |
| 5,147,377 A | 9/1992 | Sahota | |
| 5,154,725 A | 10/1992 | Leopold | |
| 5,156,594 A | 10/1992 | Keith | |
| 5,156,612 A | 10/1992 | Pinchuk et al. | |
| 5,158,548 A | 10/1992 | Lau et al. | |
| 5,159,937 A | 11/1992 | Tremulis | |
| 5,171,230 A | 12/1992 | Eland et al. | |
| 5,176,637 A | 1/1993 | Sagae | |
| 5,180,585 A | 1/1993 | Jacobson et al. | |
| 5,192,290 A | 3/1993 | Hilal | |
| 5,209,728 A | 5/1993 | Kraus et al. | |
| 5,213,574 A | 5/1993 | Tucker | |
| 5,221,257 A * | 6/1993 | Rosenbloom et al. | 604/510 |
| 5,221,270 A | 6/1993 | Parker | |
| 5,226,888 A | 7/1993 | Arney | |
| 5,234,416 A | 8/1993 | Macaulay et al. | |
| 5,240,537 A | 8/1993 | Bodicky | |
| 5,246,420 A | 9/1993 | Kraus et al. | |
| 5,254,091 A | 10/1993 | Aliahmad et al. | |
| 5,256,144 A | 10/1993 | Kraus et al. | |
| 5,258,160 A | 11/1993 | Utsumi et al. | |
| 5,259,839 A | 11/1993 | Burns | |
| 5,270,086 A | 12/1993 | Hamlin | |
| 5,279,561 A | 1/1994 | Roucher et al. | |
| 5,279,562 A | 1/1994 | Sirhan et al. | |
| 5,304,134 A | 4/1994 | Kraus et al. | |
| 5,304,198 A | 4/1994 | Samson | |
| 5,313,934 A * | 5/1994 | Wiita et al. | 600/109 |
| 5,316,706 A | 5/1994 | Muni et al. | |
| 5,318,032 A | 6/1994 | Lonsbury et al. | |
| 5,318,527 A | 6/1994 | Hyde et al. | |
| 5,318,532 A | 6/1994 | Frassica | |
| 5,320,604 A | 6/1994 | Walker et al. | |
| 5,324,259 A | 6/1994 | Taylor et al. | |
| 5,324,263 A | 6/1994 | Kraus et al. | |
| 5,328,468 A | 7/1994 | Kaneko et al. | |
| 5,334,148 A | 8/1994 | Martin | |
| 5,334,168 A | 8/1994 | Hemmer | |
| 5,335,410 A | 8/1994 | Burnham | |
| 5,342,386 A | 8/1994 | Trotta | |
| 5,344,400 A | 9/1994 | Kaneko et al. | |
| 5,346,505 A | 9/1994 | Leopold | |
| 5,370,615 A | 12/1994 | Johnson | |
| 5,370,655 A | 12/1994 | Burns | |
| 5,375,589 A * | 12/1994 | Bhatta | 600/104 |
| 5,387,193 A | 2/1995 | Miraki | |
| 5,389,087 A | 2/1995 | Miraki | |
| 5,397,306 A | 3/1995 | Nobuyoshi et al. | |
| 5,399,164 A | 3/1995 | Snoke et al. | |
| 5,403,292 A | 4/1995 | Ju | |
| 5,405,338 A | 4/1995 | Kranys | |
| 5,411,477 A | 5/1995 | Saab | |
| 5,423,754 A | 6/1995 | Cornelius et al. | |
| 5,425,709 A | 6/1995 | Gambale | |
| 5,425,712 A | 6/1995 | Goodin | |
| 5,425,735 A | 6/1995 | Rosen et al. | |
| 5,441,484 A | 8/1995 | Atkinson et al. | |
| 5,447,503 A | 9/1995 | Miller | |
| 5,454,795 A | 10/1995 | Samson | |
| 5,458,613 A | 10/1995 | Gharibadeh et al. | |
| 5,470,322 A | 11/1995 | Horzewski et al. | |
| 5,480,383 A | 1/1996 | Bagnoisan et al. | |
| 5,496,271 A | 3/1996 | Burton et al. | |
| 5,496,292 A * | 3/1996 | Burnham | 604/526 |
| 5,496,294 A | 3/1996 | Hergenrother et al. | |
| 5,503,263 A | 4/1996 | Watanabe | |
| 5,509,910 A | 4/1996 | Lunn | |
| 5,514,112 A * | 5/1996 | Chu et al. | 604/267 |
| 5,531,715 A | 7/1996 | Engelson et al. | |
| 5,538,513 A | 7/1996 | Okajima | |
| 5,540,236 A | 7/1996 | Ginn | |
| 5,542,924 A | 8/1996 | Snoke et al. | |
| 5,542,937 A | 8/1996 | Chee et al. | |
| 5,549,552 A | 8/1996 | Peters et al. | |
| 5,549,556 A | 8/1996 | Ndondo-Lay et al. | |
| 5,554,121 A | 9/1996 | Ainsworth et al. | |
| 5,554,139 A | 9/1996 | Okajima | |
| 5,569,200 A | 10/1996 | Umeno et al. | |
| 5,569,218 A | 10/1996 | Berg | |
| 5,588,965 A | 12/1996 | Burton et al. | |
| 5,591,129 A | 1/1997 | Shoup et al. | |
| 5,605,543 A | 2/1997 | Swanson | |
| 5,606,979 A | 3/1997 | Hodgson | |
| 5,628,733 A * | 5/1997 | Zinreich et al. | 604/267 |
| 5,643,209 A | 7/1997 | Fugoso et al. | |
| 5,643,298 A | 7/1997 | Nordgren et al. | |
| 5,645,528 A | 7/1997 | Thome | |
| 5,649,908 A | 7/1997 | Itoh | |
| 5,653,696 A * | 8/1997 | Shiber | 604/267 |
| 5,674,098 A | 10/1997 | Inaba et al. | |
| 5,702,439 A | 12/1997 | Keith et al. | |
| 5,716,373 A | 2/1998 | Wolvek et al. | |
| 5,718,686 A | 2/1998 | Davis | |
| 5,725,513 A | 3/1998 | Ju et al. | |
| 5,728,063 A | 3/1998 | Preissman et al. | |
| 5,743,876 A | 4/1998 | Swanson | |
| 5,762,637 A | 6/1998 | Berg et al. | |

| | | | |
|---|---|---|---|
| 5,772,609 A | 6/1998 | Nguyen et al. | |
| 5,792,114 A | 8/1998 | Fiore et al. | |
| 5,843,050 A | 12/1998 | Jones et al. | |
| 5,891,110 A | 4/1999 | Larson et al. | |
| 5,944,712 A | 8/1999 | Frassica et al. | |
| 5,971,955 A | 10/1999 | Nap et al. | |
| 5,993,424 A | 11/1999 | Lorenzo et al. | |
| 6,048,338 A | 4/2000 | Larson et al. | |
| 6,102,891 A | 8/2000 | van Earp | |
| 6,113,579 A | 9/2000 | Eidenschink et al. | |
| 6,139,510 A | 10/2000 | Palermo | |
| 6,183,450 B1 * | 2/2001 | Lois | 604/267 |
| 6,287,320 B1 | 9/2001 | Slepian | |
| 6,458,119 B1 * | 10/2002 | Berenstein et al. | 606/1 |
| 6,517,515 B1 | 2/2003 | Eidenschink | |
| 6,623,504 B2 | 9/2003 | Vrba et al. | |
| 6,652,507 B2 | 11/2003 | Pepin | |
| 6,790,221 B2 | 9/2004 | Monroe et al. | |
| 6,860,696 B2 * | 3/2005 | Bazan | 414/403 |
| 2002/0121472 A1 * | 9/2002 | Garner et al. | 210/348 |
| 2004/0073158 A1 | 4/2004 | Shah et al. | |
| 2005/0234426 A1 * | 10/2005 | Weber et al. | 604/523 |
| 2006/0052767 A1 * | 3/2006 | Weber et al. | 604/523 |

FOREIGN PATENT DOCUMENTS

| | | |
|---|---|---|
| DE | 35 28 876 A1 | 2/1987 |
| EP | 0 171 884 A1 | 2/1986 |
| EP | 0 237 564 B1 | 9/1987 |
| EP | 0 448 886 A1 | 10/1991 |
| EP | 0 452 595 A1 | 10/1991 |
| EP | 0 452 901 B1 | 10/1991 |
| EP | 0 594 201 A2 | 4/1994 |
| EP | 0 688 576 A1 | 12/1995 |
| WO | WO 93/04726 A1 | 3/1993 |
| WO | WO 93/17750 A1 | 9/1993 |
| WO | WO 94/01160 A1 | 1/1994 |
| WO | WO 96/03092 A1 | 2/1996 |
| WO | WO 96/38193 A1 | 12/1996 |
| WO | WO 96/39205 A2 | 12/1996 |
| WO | WO 96/39219 A1 | 12/1996 |
| WO | WO 99/48548 A1 | 9/1999 |
| WO | WO 00/45885 A1 | 8/2000 |

OTHER PUBLICATIONS

Kohan, *Nylon Plastics Handbook*, Hanser/Gardner Publications, Inc., Cincinnati, Ohio, Copyright 1995, pp. 378-387.

* cited by examiner

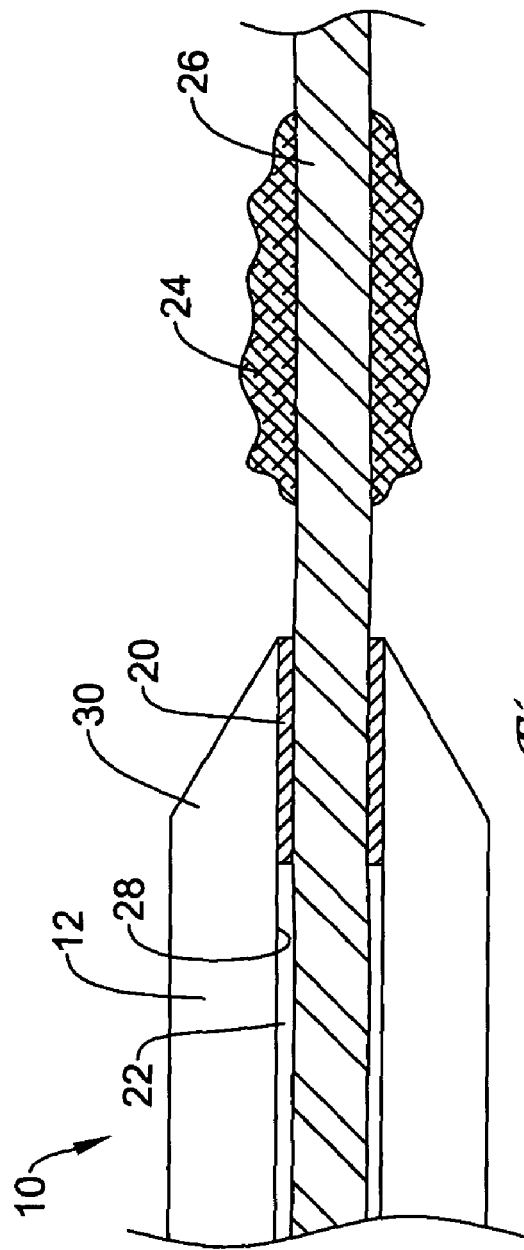
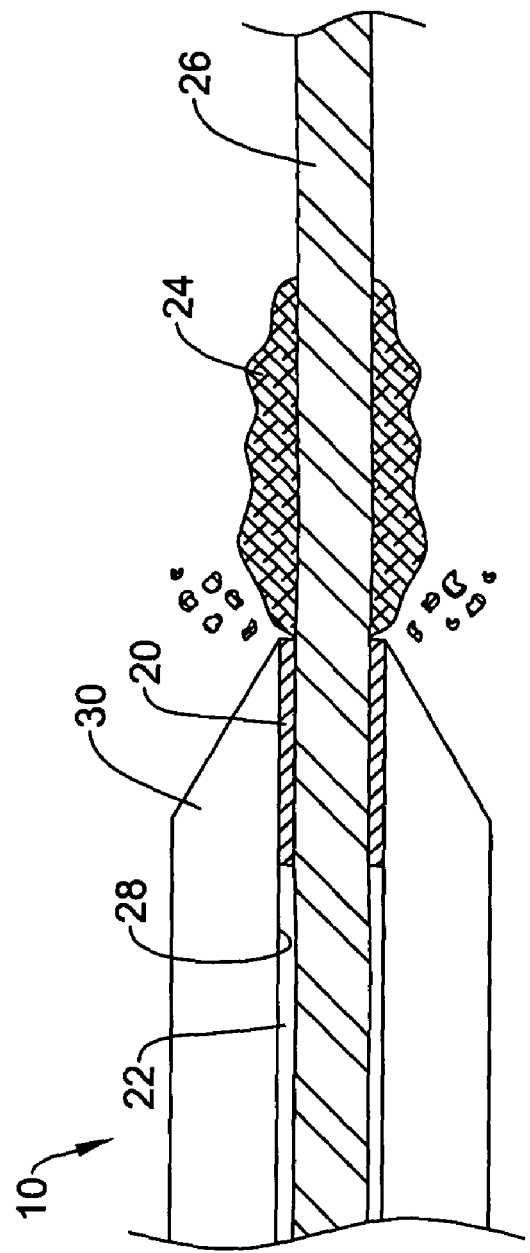

CATHETER TIP TO REDUCE WIRE LOCK

FIELD OF THE INVENTION

The invention relates to intracorporal medical devices, for example, intravascular medical devices. More particularly, the invention relates to intravascular catheters that include a scraping member that can be used, for example, to chafe or scrape debris from a guidewire and reduce the incidence of wire lock.

BACKGROUND

A wide variety of medical devices have been developed for medical use, for example, intravascular use. Some of these devices include catheters, guidewires, and other such devices that have certain characteristics. Of the known medical devices, each has certain advantages and disadvantages. There is an ongoing need to provide alternative designs and methods of making and using medical devices.

BRIEF SUMMARY

The invention provides design, material, and manufacturing method alternatives for intracorporal medical devices having a scraping member or similarly functioning structure. In at least some embodiments, the medical devices include an elongate shaft having a proximal portion, a distal portion, and a lumen extending at least a portion of the length therethrough. A scraping member may be disposed adjacent the lumen that can substantially remove debris, for example, from a guidewire disposed in the lumen. Methods for making and using medical devices are also disclosed. Some of these and other features and characteristics of the inventive devices and methods are described in more detail below.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a partial cross-sectional side view of an example medical device;

FIG. 3 is another partial cross-sectional side view of the medical device shown in FIG. 2;

DETAILED DESCRIPTION

Figure 1:
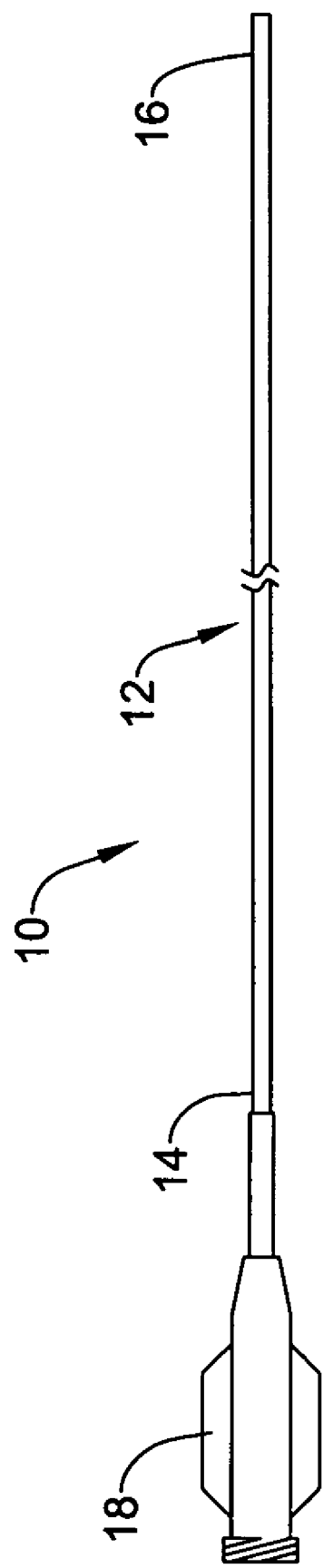
FIG. 1 is a side view of an example medical device.

The following description should be read with reference to the drawings wherein like reference numerals indicate like elements throughout the several views. The detailed description and drawings illustrate example embodiments of the claimed invention.

FIG. 1 is a side view of an example catheter 10. Catheter 10 includes a catheter shaft 12 having a proximal end region 14 and a distal end region 16. A hub or manifold 18 may be disposed adjacent proximal end region 14. One or more lumens (not shown, best seen in FIG. 2) may be defined in shaft 12 that extend between proximal end region 14 and distal end region 16.

In some embodiments, catheter 10 may be a guide catheter. However, catheter 10 need not necessarily be a guide catheter as catheter 10 can be any suitable catheter or related medical device. The use of catheter 10 may be similar to the use of typical catheters. For example, catheter 10 may be advanced through the vasculature of a patient to a location adjacent a target region. Catheter 10 may then be used for its intended purpose. For example, if catheter 10 is a guide catheter (as shown), then another diagnostic or therapeutic medical device may be advanced over or through (i.e., through a lumen defined therein) catheter 10.

During an intravascular intervention, debris (e.g., coagulated blood, contrast media, etc.) can dry on, clump on, adhere to, or otherwise become disposed on intravascular devices. If debris is clumped on a guidewire, the guidewire can become "locked" within another device such as within the guidewire lumen of a guide catheter. One of the reasons why wire lock may occur is because the distal tip of the guide catheter is frequently designed to be atraumatic and, consequently, is soft enough so that it may "stretch" when the clumped guidewire approaches the distal tip. Once the clump enters a less pliable portion of the guide catheter, the clumped guidewire becomes substantially fixed within the guidewire lumen. Once locked, it becomes more difficult to effectively use the catheter and/or guidewire. A similar phenomenon may occur with other analogous sets of medical devices.

One of the design features included in catheter 10 is the inclusion of a scraping member 20 as shown in FIG. 2. Scraping member 20 is adapted and configured to help reduce wire lock. As such, scraping member 20 is positioned within a lumen 22 defined in catheter 10 so that debris 24 disposed on a guidewire 26 can be "scraped off" or otherwise substantially removed from guidewire 26 by scraping member 20 as illustrated in FIG. 3. Scraping occurs when scraping member 20 comes into contact with debris 24 on guidewire 26. This may happen either by advancing catheter 10 over guidewire 26 so as to initiate contact between scraping member 20 and debris 24 or by retracting guidewire 26 in a manner that initiates contact. By releasing debris 24 from guidewire 26, wire lock is substantially reduced. Catheter 10 may analogously be any other device that can be used in combination with a second medical device to scrape or otherwise remove debris from the second device. In addition to providing scraping of debris, scraping member 20 also functions to provide radial reinforcement of the distal tip region. This minimizes flaring of the tip. Flaring of the tip can allow the tip to wedge over and trap debris, increasing the risk of wire lock.

Scraping member 20 is generally positioned within lumen 22. In some embodiments, scraping member 20 is attached to an inside wall surface 28 of catheter shaft 12 and extends inward into lumen 22. According to this embodiment, the inside diameter of lumen 22 is smaller at scraping member 20 than at other positions along lumen 22. The smaller inside diameter defined by scraping member 20 is intended to have a tighter tolerance with guidewire 26. For example, the inside diameter defined by lumen 22 may be about 0.010 to about 0.020 inches, depending on the outside diameter of guidewire 26, whereas the inside diameter defined by scraping member 20 may be about 0.008 to about 0.018 inches (generally about 0.002 inches smaller than the inside diameter of lumen 22). In one particular embodiment, guidewire 26 may have an outside diameter of 0.014 inches, the inside diameter defined by lumen 22 may be about 0.018 inches, and the inside diameter defined by scraping member 20 may be about 0.015 inches.

The means for attaching or securing scraping member 20 to inside wall surface 28 may include adhesive bonding, mechanical bonding, chemical bonding, thermal bonding, and the like, or any other appropriate means. Some embodiments of catheter 10 may have scraping member 20 embedded (either in part or completely) within inside wall surface 28 or within a coating or layer of material disposed adjacent inside wall surface 28. In general, the attachment means is any means suitable for securing scraping member 20 to catheter shaft 12 so that scraping member 20 can execute the desired scraping effect.

Scraping member 20 may be made from any suitable material such as a metal, metal alloy, polymer, metal-polymer composite, and the like, or any other suitable material. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material. Polymer scraping members can include rigid polymers such as high durometer polyamide, polyimide, polyetheretherketone (PEEK) and mixtures thereof. Nanocompositions can also be utilized.

In some embodiments, scraping member 20 may be made from, doped with, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, molybdenum, palladium, tantalum, tungsten or tungsten alloy, plastic material loaded with a radiopaque filler, and the like.

Scraping member 20 may include a coating such as a hydrophobic, hydrophilic, lubricious, protective, or any other suitable type of coating. Hydrophobic coatings such as fluoropolymers provide a dry lubricity. This may improve the ability of guidewire 26 to pass through scraping member 20 and/or lumen 22. Lubricious coatings may impact the steerability and improve lesion crossing capability of catheter 10. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It is worth mentioning that distal end region 16 of catheter shaft 12, as shown in FIGS. 2-3, may include a tapered distal tip 30. Generally, tapered distal tip 30 provides an atraumatic end that is suitable for navigating through the vasculature. However, some alternatives may include a generally flat (i.e., not tapered) tip or a tip having different properties. A person of skill in the art is familiar with the various types and configurations of catheter tips that would be suitable for use with catheter 10 without departing from the spirit of the invention.

Figure 4:
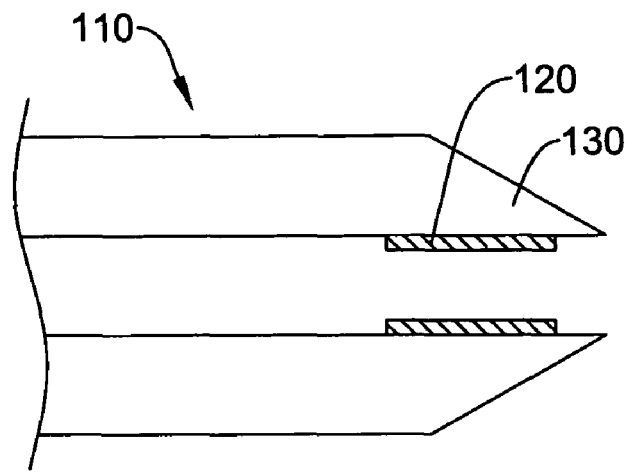
FIG. 4 is a partial cross-sectional side view of another example medical device.

FIGS. 4-10 depict alternative embodiments of catheter 10 that include various scraping members. Guidewire 26 and debris 24 have been omitted from these drawing so that design of the various medical devices can be more fully appreciated. Turning now to FIG. 4, this figure depicts catheter 110 with scraping member 120 that is set back a distance from distal tip 130 (i.e., set back from the distal-most end of distal tip 130). This embodiment illustrates that although scraping member 120 is generally positioned near distal tip 130, the precise location of scraping member 120 may vary. The set back distance from the distal tip can be about 0.5 mm to about 5.0 mm to help maintain an atraumatic tip while preventing wire lock near the distal end. In addition, other dimensional aspects of this and other scraping members 120 may vary. For example, scraping member 120 may have a length of about 0.05 mm to about 10.0 mm.

Figure 5:
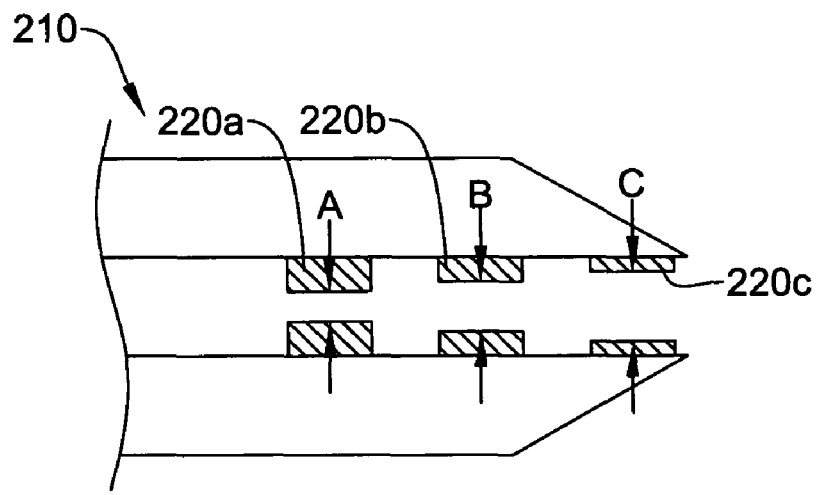
FIG. 5 is a partial cross-sectional side view of another example medical device.

FIG. 5 illustrates catheter 210 that includes multiple scraping members 220 (indicated in FIG. 5 as scraping members 220a, 220b, and 220c). Not only does catheter 210 include multiple scraping members 220a/b/c, but the sizes of the scraping members 220a/b/c also vary. The various sizes impact the inside diameter that is defined adjacent the particular scraping member. For example, scraping member 220a defines an inside diameter A, whereas scraping member 220b defines an inside diameter B, and scraping member 220c defines an inside diameter C. The various inside diameters are shown in FIG. 5 to increase along the distal direction (i.e., C>B>A). However, this is not the only available arrangement. For example, the inside diameters may increase along the proximal direction (i.e., A>B>C), the inside diameters may all be the same, or the inside diameters may vary in any other alternative manner. One reason why it may be desirable to have multiple scraping members 220a/b/c that have different sizes is so that guidewire 26 can be scraped in a more gradual or step-wise manner. Alternatively, a single scraping member having a tapered or stepped inside diameter can be utilized and provide the same function.

Figure 6:
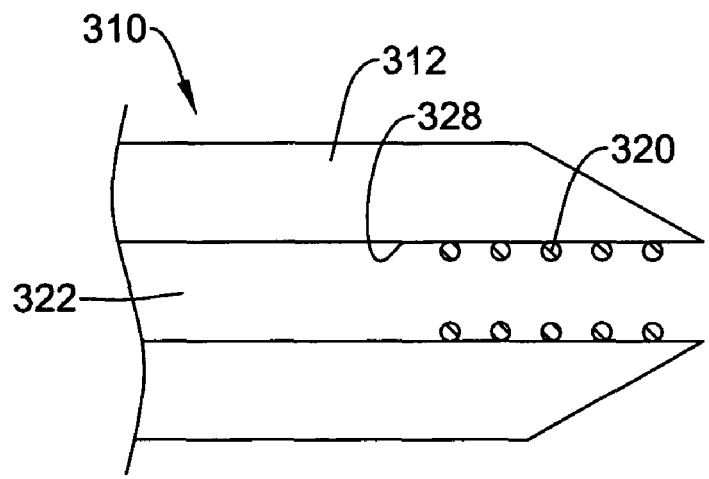
FIG. 6 is a partial cross-sectional side view of another example medical device.

The scraping members previously presented all were shown to have a generally tubular shape. However, this is not intended to limit the scope of the invention to any particularly shaped scraping member. FIG. 6 is intended to demonstrate that any suitable shape or configuration may be utilized. For example, FIG. 6 illustrates another example catheter 310 where scraping member 320 is a coil or has a coil-like shape. As such, scraping member 320 may be disposed along inner wall surface 328 of catheter shaft 312 and extend inward into lumen 322. Just like any of the other scraping members disclosed herein, scraping member 320 may be made of metals, metal alloys, polymers, metal-polymer composites, and the like, and scraping member 320 may include a coating.

Figure 7:
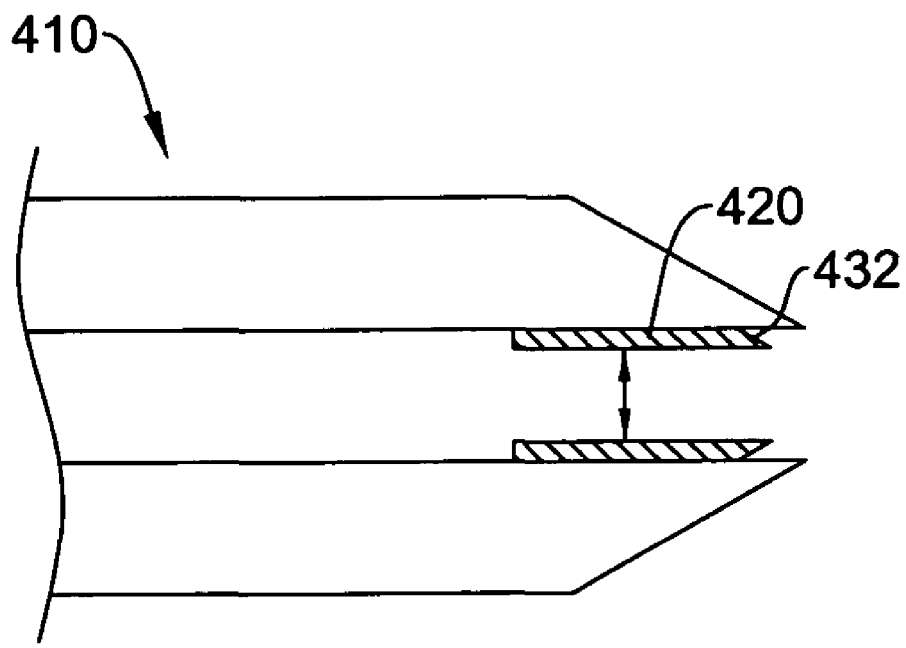
FIG. 7 is a partial cross-sectional side view of another example medical device.

FIG. 7 depicts catheter 410 wherein scraping member 420 includes a tapered or wedge-like leading edge 432. Tapered leading edge 432 may improve the debris-removing ability of scraping member 420. This is because the wedge-like leading edge 432 may be able more easily break up and remove debris 24 from guidewire 26. The pitch or steepness of the wedge-like edge 432 may vary depending on the particular intervention. Any of the other design variations described herein may be analogously incorporated into scraping member 420 and/or catheter 410.

Figure 8:
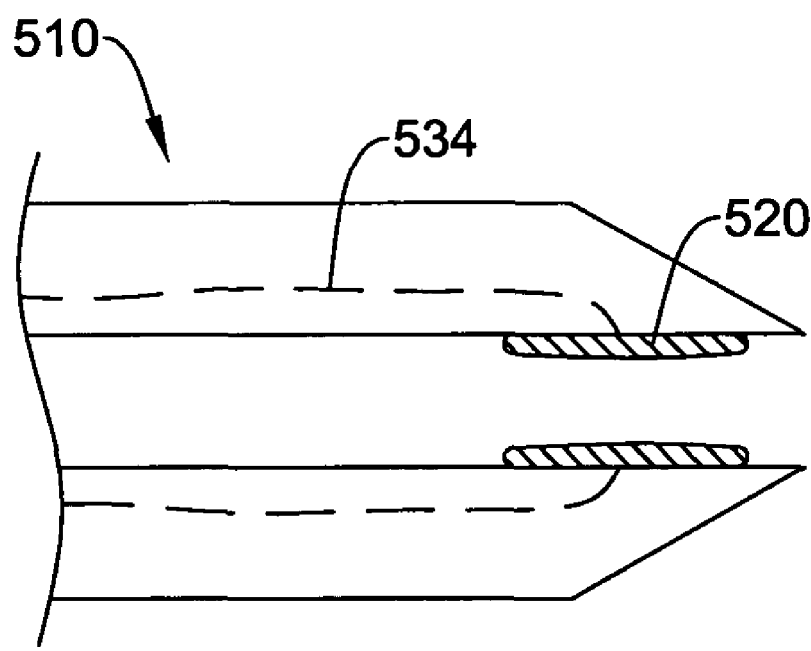
FIG. 8 is a partial cross-sectional side view of another example medical device.

FIG. 8 illustrates catheter 510 wherein scraping member 520 is inflatable via an inflation lumen 534. The design of catheter 510 is akin to an angioplasty balloon catheter except that the "balloon" (i.e., the inflatable scraping member 520) is positioned along the interior of catheter 510 rather than along an outside wall surface. Because of the similarity between catheter 510 and typical angioplasty balloon catheters, the configuration of inflation lumen 534 may be generally similar to the analogous inflation lumens of balloon catheters. In addition, a suitable inflation media (e.g., angioplasty balloon inflation media or the like) may be passed through lumen 534 into scraping member 520. By including an inflatable scraping member 520, catheter 510 desirably is able to both be usable with a variety of different guidewires and also provide the desired scraping feature. This allows catheter 510 to "scrape" a variety of guidewires having a variety of outside diameters.

Figure 9:
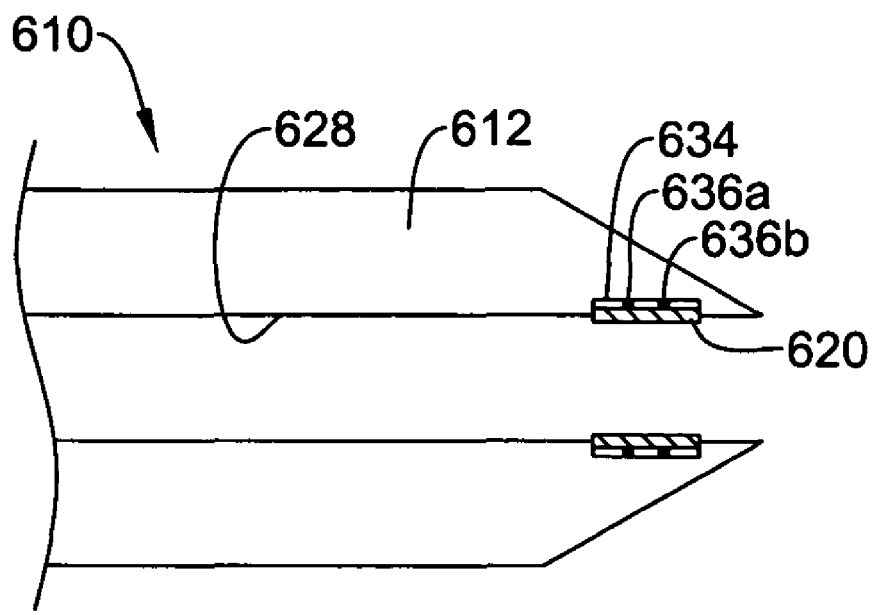
FIG. 9 is a partial cross-sectional side view of another example medical device.
Figure 10:
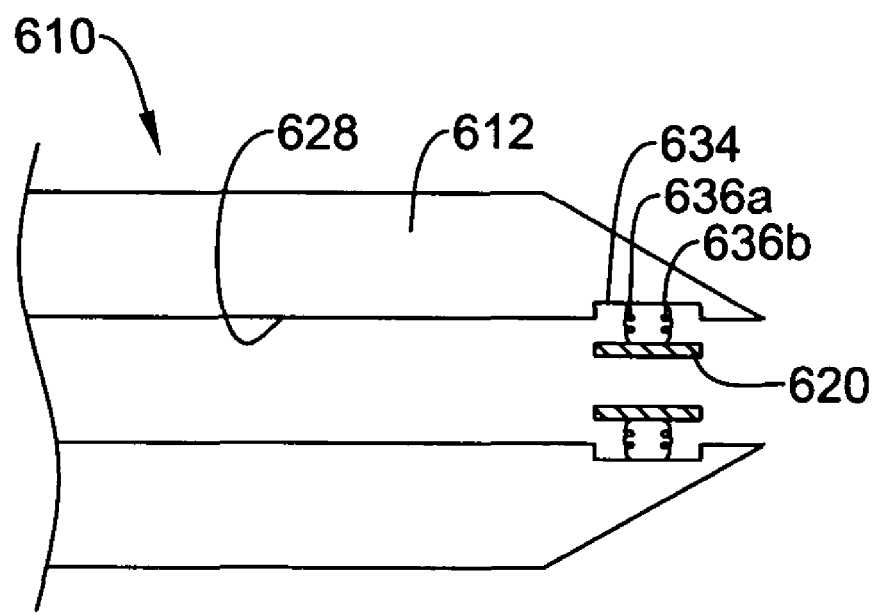
FIG. 10 is another partial cross-sectional side view of the example medical device shown in FIG. 9.

FIGS. 9 and 10 illustrate catheter 610 wherein scraping member 620 is inset within a groove 634 defined along inside wall surface 628 of catheter shaft 612 and includes one or more springs 636 (shown in FIGS. 9-10 as springs 636*a* and 636*b*) extending between scraping member 620 and groove 634. By including springs 636, scraping member 620 is configured to shift between a first configuration wherein the scraping member 620 defines the largest inside diameter (thus, being configured to accommodate guidewires having larger outside diameters), a second configuration wherein the scraping member 620 defines the largest inside diameter as seen in FIG. 10 (thus, being configured to accommodate guidewires having smaller outside diameters), and anywhere in between.

Springs 636*a/b* may be biased to exert inward force onto scraping member 620. However, passing another device such as guidewire 26 through lumen 622 and into contact with scraping member 620 is sufficient to overcome the bias enough that the device may pass through scraping member 620. However, enough inward force remains so that scraping member 620 can still remove debris 24 from guidewire 26.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An intravascular catheter and guidewire system designed for reducing guidewire lock, comprising:
   an elongate tubular member having a proximal portion, a distal portion, an inner wall surface, and a lumen having a first inner diameter defined along the inner wall surface;
   a guidewire slidably disposed in the lumen, the guidewire having an outside diameter;
   a hub disposed adjacent the proximal portion of the tubular member; and
   a tubular rigid scraping member, the rigid scraping member having a second inner diameter and a continuous inner wall surface and a continuous outer surface, the outer surface of the rigid scraping member disposed along the inner wall surface of the tubular member adjacent the distal portion of the tubular member and extending into the lumen, wherein the scraping member is configured to provide radial reinforcement of the distal portion;
   wherein the first inner diameter is approximately 0.010 inches to 0.020 inches and the second diameter is approximately 0.008 inches to 0.018 inches; and
   wherein the second inner diameter of the scraping member has a first tolerance with the outside diameter of the guidewire, wherein the first inner diameter of the guidewire lumen has a second tolerance with the outside diameter of the guidewire, and wherein the first tolerance is tighter than the second tolerance.

2. The medical device of claim 1, wherein the distal portion includes a distal end and wherein the scraping member is disposed at the distal end.

3. The medical device of claim 1, wherein the distal portion includes a distal end and wherein the scraping member is disposed proximally of the distal end.

4. The medical device of claim 1, wherein the scraping member includes a tapered inside diameter.

5. The medical device of claim 1, wherein the inside diameter of the scraping member is less than the inside diameter of the lumen.

6. The medical device of claim 1, wherein the inside diameter of the scraping member is substantially equal to the inside diameter of the lumen.

7. The medical device of claim 1, wherein the scraping member includes a tapered leading edge.

8. The medical device of claim 1, wherein the scraping member is inset within a groove defined along the inner wall surface.

9. The medical device of claim 1, wherein the scraping member is adapted to define a variety of inside diameters.

10. The medical device of claim 1, wherein the scraping member includes a lubricious coating disposed on the inner wall surface.

11. The medical device of claim 1, wherein the scraping member includes a metal, metal alloy, or polymer.

12. The medical device of claim 11, wherein the scraping member includes a radiopaque material.

13. The medical device of claim 1, further comprising one or more additional scraping members and wherein each of the scraping members has an inside diameter.

14. The medical device of claim 13, wherein each scraping member has substantially the same inside diameter.

15. The medical device of claim 13, wherein at least two of the scraping members have different inside diameters.

16. The medical device of claim 15, wherein the scraping members each have an inside diameter and wherein the inside diameter of a first scraping member is greater than the inside diameter of a second scraping member positioned distally of the first scraping member.

* * * * *